(12) United States Patent
Rath

(10) Patent No.: US 6,693,129 B2
(45) Date of Patent: Feb. 17, 2004

(54) COMPOSITIONS AND METHODS FOR LOWERING PLASMA LIPOPROTEIN(A) AND RISK FACTORS OF CARDIOVASCULAR DISEASES

(75) Inventor: Matthias Rath, Twentepoort Oost 3, NL-7609 RG Almelo (NL)

(73) Assignee: Matthias Rath, Santa Clara, CA (US)

( * ) Notice: Subject to any disclaimer, the term of this patent is extended or adjusted under 35 U.S.C. 154(b) by 0 days.

(21) Appl. No.: 09/970,609

(22) Filed: Oct. 3, 2001

(65) Prior Publication Data

US 2002/0094996 A1 Jul. 18, 2002

Related U.S. Application Data

(60) Provisional application No. 60/237,186, filed on Oct. 3, 2000.

(51) Int. Cl.⁷ ................... A61K 31/34; A61K 31/20; A61K 31/44; A61K 31/355; A61K 31/195
(52) U.S. Cl. ................... 514/474; 514/458; 514/564; 514/565; 514/725; 514/251; 514/249; 514/562; 514/356
(58) Field of Search ................ 514/474, 725, 514/458, 249, 251, 168, 171, 188; 424/655, 641, 630, 639, 640, 602, 614

(56) References Cited

U.S. PATENT DOCUMENTS

| | | | | |
|---|---|---|---|---|
| 4,009,265 A | * | 2/1977 | Howard | 424/177 |
| 4,414,238 A | * | 11/1983 | Schmidl | 426/602 |
| 4,657,866 A | * | 4/1987 | Kumar | 435/240 |
| 4,891,220 A | | 1/1990 | Donzis | 424/88 |
| 5,108,767 A | * | 4/1992 | Mulchandani et al. | 426/72 |
| 5,230,996 A | * | 7/1993 | Rath et al. | 435/1.1 |
| 5,268,181 A | | 12/1993 | Neill et al. | 424/465 |
| 5,278,189 A | | 1/1994 | Rath et al. | 514/561 |
| 5,326,569 A | * | 7/1994 | Acosta et al. | 424/440 |
| 5,332,579 A | * | 7/1994 | Umbdenstock | 424/639 |
| 5,650,418 A | | 7/1997 | Rath et al. | 514/356 |
| 5,922,766 A | * | 7/1999 | Acosta et al. | 514/561 |
| 5,962,517 A | * | 10/1999 | Murad | 514/474 |
| 6,048,846 A | * | 4/2000 | Cochran | 514/168 |
| 6,245,803 B1 | * | 6/2001 | Acosta et al. | 514/440 |
| 6,299,896 B1 | * | 10/2001 | Cooper et al. | 424/441 |
| 6,361,800 B1 | * | 3/2002 | Cooper et al. | 424/630 |
| 6,451,341 B1 | * | 9/2002 | Slaga et al. | 424/468 |
| 2002/0128309 A1 | * | 9/2002 | Rath | 514/458 |
| 2002/0173546 A1 | * | 11/2002 | Rath et al. | 514/561 |
| 2003/0003162 A1 | * | 1/2003 | Rath | 424/682 |

FOREIGN PATENT DOCUMENTS

| | | | |
|---|---|---|---|
| EP | 0891771 A1 | * | 1/1999 |
| EP | 1068868 A2 | * | 1/2001 |
| EP | 1163904 A1 | * | 12/2001 |
| EP | 1195159 A1 | * | 10/2002 |
| GB | 2268871 A | * | 1/1994 |

OTHER PUBLICATIONS

"Life Extension Mlx Multivitamin" Product Information Brochure (www.iherb.com, 1997).*
"Multi li Caps" Product Information Brochure (www.solgar.com, 1996).*
"Mega Vita–Min" Product Information Brochure (www.naturesbounty.com, 2000).*
Vinson, Joe A. et al., "A Citrus Extract Plus Ascorbic Acid Decreases Lipids, Lipid Peroxides, Lipoprotein Oxidative Susceptibility, and Atherosclerosis in Hypercholesterolemic Hamsters" *J. Agric. Food Chem*, vol. 46, pp. 1453–1459, 1998.
Giroux,Isabelle et al., "Role of dietary lysine, methionine, and arginine in the regulation of hypercholesterolemia in rabbits" *J. Nutr. Biochem.*, vol. 10, pp. 166–171, 1991.

* cited by examiner

Primary Examiner—Zohreh Fay
Assistant Examiner—Brian-Yong S. Kwon
(74) Attorney, Agent, or Firm—Kenyon & Kenyon

(57) ABSTRACT

The present invention provides compositions and methods for lowering plasma Lp(a) levels in humans. The present invention provides compositions and methods for lowering the risk factors for cardiovascular diseases. Moreover, this invention provides therapeutic alternatives to current pharmaceutical interventions for the lowering of cholesterol, LDL-cholesterol, triglycerides and other metabolic risk factors.

6 Claims, 1 Drawing Sheet

COMPOSITIONS AND METHODS FOR LOWERING PLASMA LIPOPROTEIN(A) AND RISK FACTORS OF CARDIOVASCULAR DISEASES

CROSS-REFERENCE TO RELATED APPLICATION

This application claims the benefits of Provisional Application Serial No. 60/237,186, filed Oct. 3, 2000, the disclosure of which is incorporated by reference in its entirety herein.

FIELD OF THE INVENTION

This invention relates to compositions and methods for lowering plasma lipoprotein(a) in humans and reducing the risk factors of cardiovascular diseases.

BACKGROUND OF THE INVENTION

Cardiovascular disease is the number one cause of death in the industrialized world. According to the World Health Organization, more than 12 million people suffer each year from heart attacks and strokes. Controlling the risk factors for cardiovascular disease is a key preventive and therapeutic target in reducing this high mortality rate. Well-established risk factors for cardiovascular disease include elevated plasma levels for cholesterol (hypercholesterolemia), triglycerides, homocysteine, and certain lipoproteins (such as low-density lipoprotein (LDL) and lipoprotein(a) [hereinafter abbreviated as "Lp(a)"].

The majority of blood lipids are transported in plasma bound to lipoprotein particles. Lipoproteins are high molecular weight carriers of plasma cholesterol and triglycerides in the form of cholesteryl esters. They are micellar lipid-protein complexes which comprise one or more proteins associated with polar lipids surrounding a cholesterol-containing core. Five major density classes of lipoproteins have been recognized: chylomicrons, very low-density lipoproteins (VLDL), intermediate density lipoprotein (IDL) low-density lipoproteins (LDL) and high-density lipoproteins (HDL).

In addition to these five major classes of lipoproteins, Lp(a) has been identified. The structure of Lp(a) is closely related to LDL in that it consists LDL with an additional disulfide linked apolipoprotein(a), also known as "apo(a)", which is a high-molecular weight adhesive protein. Apo(a) is in turn covalently bound to glycoprotein Apo B100, also known as "apolipoprotein B-100", which is an integral part of LDL. While Apo B100 allows the LDL molecule to carry the hydrophobic cholesterol in the plasma and tissue fluids, apo(a) is water soluble and does not bind lipid. The major site of synthesis of plasma apo(a) appears to be the liver. It is presently unknown as to where Lp(a) is assembled. Lp(a) cholesterol appears to be a bad form of cholesterol, since elevated Lp(a) have been associated with the development of atherosclerosis, coronary heart disease, myocardial infraction, cerebral infarction, and restenosis following balloon angioplasty.

The structure of Lp(a) shares high homology to that of plasminogen, providing a linkage between the atherogenesis and clotting system. It has been hypothesized that Lp(a) can inhibit the fibrinolysis system. Lp(a) is shown to bind competitively to the plasminogen binding site and reduces the amount of plasmin generated by tissue plasminogen activator. Furthermore, Lp(a) is shown to be able to bind to fibrin and may prevent degradation of an existing thrombus by plasmin.

Among various lipoproteins, Lp(a) is often associated with the highest risk for cardiovascular disease. Several facts about Lp(a) are particularly noteworthy in connection with this invention (for review see: Rath, M. et al., "Detection and Quantification of Lipoprotein(a) in the Arterial Wall of 107 Coronary Bypass Patients," Arteriosclerosis 9: 579–592 (1989), incorporated herein by reference in its entirety. For example, Lp(a) selectively accumulates in atherosclerotic plaques and contributes to the size of these plaques eventually leading to heart attacks and strokes; and the amount of Lp(a) deposited inside the artery walls is dependent from the plasma level of this lipoprotein. Studies have shown that Lp(a) bonded to glycosaminoglycan is more ingestible by a macrophage and may hence be considered to act for the promotion of conversion into foam cells.

In view of these, Lp(a) is considered to play a role in the onset and deterioration of arteriosclerosis. For ischemic heart diseases, cerebral infraction, carotid sclerosis, cerebrovascular dementia and diabetes, Lp(a) is considered to be detrimental factor.

Thus, lowering plasma levels of Lp(a) becomes a desirable therapeutic target that can reduce the risk for cardiovascular diseases in millions of people.

Despite the widely held belief that the individual plasma levels of Lp(a) are largely determined by genetic factors, there are reports showing different compounds used to affect its plasma level in humans. It has been reported that steroid hormones can lower plasma levels of Lp(a). For example, Lp(a) plasma concentrations have been shown to be influenced by the administration of anabolic steroids, progesterone and estrogen in postmenopausal women. Estrogen therapy in males with prostatic cancer reduced 50% of the plasma Lp(a). European published patent application 0 605 193 discloses anti-estrogenic and anti-androgenic agents in lowering total cholesterol and LDL levels in serum. U.S. Pat. No. 5,668,162 describes an anti-bacteria and anti-septic compound, isothiazolones, in lowering plasma Lp(a). U.S. Pat. No. 5,607,965 describes a condensed tannin existing in plants, known as proanthocyanidine, that possesses Lp(a) lowering activity. U.S. Pat. No. 5,489,611 describes organic compound, retinoids, in lowering Lp(a) levels. However, all of these compounds have significant side-effects that render their utility for long-term administration in humans questionable.

U.S. Pat. No. 5,627,172 describes creatine derivatives in lowering plasma cholesterol, lipids or lipoproteins. There is, however, no showing of this compound on plasma Lp(a). U.S. Pat. No. 5,929,091 describes a method for lowering plasma Lp(a) by inhibiting microsomal triglyceride transfer. All of the above patents are hereby incorporated in full by reference.

A safe composition therapy that can lower plasma Lp(a) is in need. We have now discovered a composition of biochemical compounds that is effective in lowering plasma Lp(a) in humans.

SUMMARY OF THE INVENTION

An object of the present invention is to provide suitable pharmaceutical treatment available that can be recommended as a preventive and therapeutic agent for effective, safe and long-term lowering of plasma Lp(a).

Another object of the present invention is to provide therapeutic alternatives to current pharmaceutical interventions—generally associated with side effects—for the lowering of cholesterol, LDL-cholesterol, triglycerides and/or other metabolic risk factors.

Another object of the present invention is to provide a Lp(a) lowering biochemical composition that exhibits remarkable lowering effects of plasma Lp(a).

Another object of the present invention is to provide methods for correcting the dysfunction of hepatocyte metabolism and hence lowering plasma Lp(a).

Another object of the present invention is to provide methods for correcting dysfunction of hepatocyte metabolism and reduce risk factors primarily produced in the liver, such as LDL-cholesterol, triglycerides and homocysteine.

Another object of the present invention is to provide therapeutic compositions for treating humans in which Lp(a) is associated including ischemic heart diseases, arteriosclerosis, cerebrovascular diseases and the like.

The present invention provides a composition of biochemical substances comprising ascorbic acid, niacin, lysine, and proline wherein the composition is in therapeutically effective amounts to lower plasma concentration of a lipoprotein in a mammal.

The present invention provides a composition of biochemical substances comprising ascorbic acid, ascorbyl palmitate, beta-, gamma-, delta-tocopherol-mix, beta-carotene, biotin, calcium ascorbate, calcium glycinate, caroteinoid mix, cholecalciferol, chromium glycinate, citrus bioflavonoids, coenzyme Q10, copper glycinate, cyanocobalamin, d-alpha-tocopherol, d-calcium pantothenate, dicalcium phosphate, folic acid, inositol, L-arginine, L-camitine, L-cysteine, L-lysine, L-proline, L-seleonmethionine, magnesium ascorbate, magnesium glycinate, manganese chelate, molybdenum glycinate, niacin, niacinamide, potassium chelate, pycnogenol, pyridoxine, riboflavin, thiamine, and zinc glycinate, wherein the composition is in therapeutically effective amounts to lower plasma concentration of a lipoprotein in a mammal.

The present invention provides a method of lowering plasma concentration of a lipoprotein in a mammal, comprising administering to the mammal a composition of biochemical substances comprising ascorbic acid, niacin, lysine, and proline, wherein the composition is in therapeutically effective amounts to lower the plasma concentration of the lipoprotein in the mammal.

The present invention provides a method of lowering plasma concentration of a lipoprotein in a mammal, comprising administering to the mammal a composition of biochemical substances comprising ascorbic acid, ascorbyl palmitate, beta-, gamma-, delta-tocopherol-mix, beta-carotene, biotin, calcium ascorbate, calcium glycinate, caroteinoid mix, cholecalciferol, chromium glycinate, citrus bioflavonoids, coenzyme Q10, copper glycinate, cyanocobalamin, d-alpha-tocopherol, d-calcium pantothenate, dicalcium phosphate, folic acid, inositol, L-arginine, L-camitine, L-cysteine, L-lysine, L-proline, L-seleonmethionine, magnesium ascorbate, magnesium glycinate, manganese chelate, molybdenum glycinate, niacin, niacinamide, potassium chelate, pycnogenol, pyridoxine, riboflavin, thiamine, and zinc glycinate, wherein the composition is in therapeutically effective amounts to lower the plasma concentration of the lipoprotein in the mammal.

DETAILED DESCRIPTION OF THE INVENTION

Figure 1:
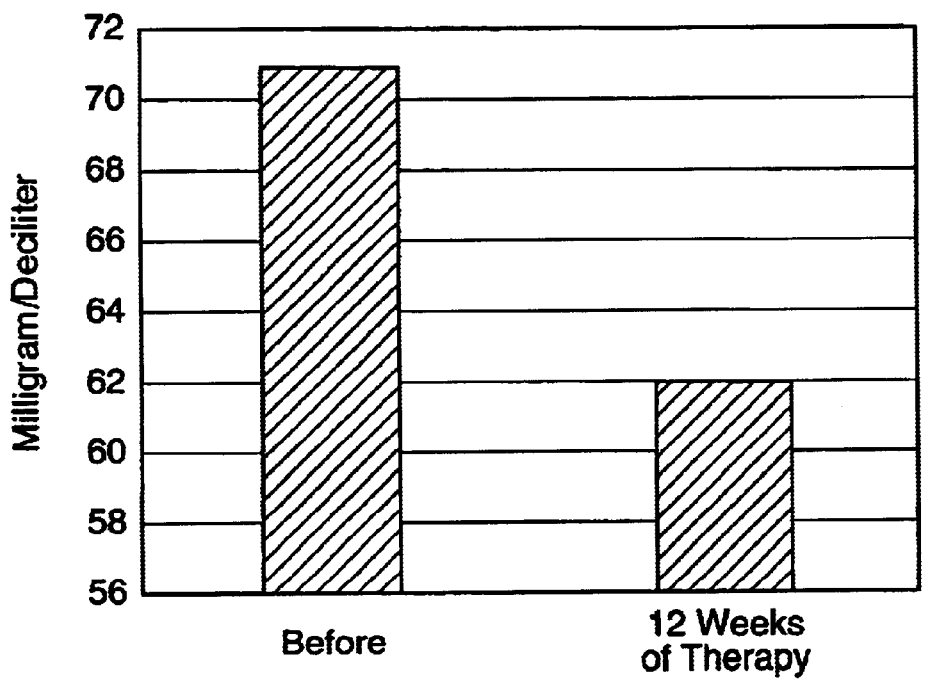
FIG. 1 depicts the change in plasma concentrations of Lp(a) in humans before and after 12 weeks of therapy.

The following definitions are provided for some of the terms used throughout this specification.

As used herein, "normal Lp(a) concentration" refers to an average plasma Lp(a) concentration below 25 mg/dl.

As used herein, "elevated Lp(a) concentration" refers to an average plasma Lp(a) concentration above 25 mg/dl.

As used herein, "acute elevation of Lp (a) concentration" refers to an average plasma Lp(a) concentration above 25 mg/dl less than the course of a week.

As used herein, "chronic elevated Lp(a ) concentration" refers to an average plasma Lp(a) concentration above 25 mg/dl more than the course of a week.

As used herein, "total-cholesterol" refers to a summation of cholesterol in plasma that are contained in the major plasma lipoproteins such as chylomicrons, VLDL, LDL and HDL.

As used herein, "LDL-cholesterol" refers to cholesterol contained in plasma LDL lipoprotein.

As used herein, "cardiovascular diseases", in the context of the present invention, refers to those disease states associated with high levels of Lp(a) in plasma as well as other lipoproteins such as LDL; and includes, inter alia, arteriosclerosis, atherosclerosis, coronary artery disease, peripheral artery disease, myocardial infarction, stroke, restenosis and bypass graft stenosis.

As used herein, the term "an effective amount" used herein refers to that an amount of the biochemical composition disclosed in this application, when administered to a human subject in need thereof, is sufficient to lower plasma Lp(a) concentration or inhibit the generation of apo(a), or reduce plasma concentrations of other lipoproteins.

As used herein, the term "therapeutically effective amount" used herein refers to an amount of biochemical composition disclosed in this application, which when administered to a human subject in need thereof, is sufficient to effect treatment for disease states alleviated by the reduction of Lp(a) or other lipoproteins. The therapeutically effective amounts can be determined routinely by one of ordinary skill in the art having regard to his/her knowledge and tho this disclosure.

As used herein, the term "treatment" refers to treating a disease state in human, which disease state is alleviated by the reduction of plasma levels of Lp(a) or other lipoproteins; and include inhibition the disease or relieving the disease. "Treatment" used herein also includes preventing, inhibiting or relieving the disease state from occurring in a human.

As used herein, the term "pharmaceutically acceptable salt" refers to those salts which retain the biological effectiveness and properties of the active ingredient of the biochemical composition, which are not otherwise undesirable. Pharmaceutically acceptable salts include, but not limited to, the sodium, potassium, calcium, magnesium, aluminum and the like.

As used herein, the term "ascorbate" include any pharmaceutically acceptable salt of ascorbate, including sodium ascorbate, as well as ascorbic acid itself. The term "lysine" refers to lysine in its electrically neutral form or a pharmaceutically acceptable salt of lysine which includes lysine hydrochloride, lysine dihydrochloride, lysine succinate, lysine glutamate, and lysine orotate. The term "proline" refers to proline and proline in a pharmaceutical acceptable salt of proline which includes proline hydrochloride, proline glutamate and the like.

An increased concentration of plasma Lp(a) represents a risk factor for stroke and cardiac infarction. Since Lp(a) in plasma is exclusively produced in the liver, we concluded that the primary cause of an overproduction of Lp(a) should be an impaired metabolism in liver cells (hepatocytes). The cause of this metabolic impairment would be a deficiency of certain biochemical compounds needed as coenzymes in the Krebs-cycle, the respiration chain and for other metabolic functions in hepatocytes.

The Krebs cycle is also called the tricarboxylic acid (TCA) cycle and the citric acid cycle. It is the final common catabolic pathway for the oxidation of fuel molecules. Two carbons enter the citric acid cycle as acetyl CoA and two carbons leave as $CO_2$. In the course of the cycle, four oxidation-reduction reactions take place to yield reduction potential in the form of three molecules of NADH and one molecule of $FADH_2$. A high energy phosphate bond (GTP) is also formed.

Additional embodiments and advantages of the invention will be set forth in the description that follows, and in part will be obvious from the description, or may be learned by practice of the invention. This invention may be realized and obtained by means of the composition and method of treatment particularly pointed out from the description and drawings, and from the claims.

A composition of biochemical substances can contain at least one ascorbate compound selected from the group consisting of ascorbic acid, pharmaceutically acceptable ascorbate salts and/or mixtures thereof in combination with at least one niacin compound selected from the group of nicotinic acid, niacin amide or another niacin salt, lysine hydrochloride, or pharmaceutically acceptable lysine salts, proline hydrochloride or pharmaceutically acceptable salts thereof and/or mixtures of these compounds. The composition can be effective to lower plasma levels of lipoprotein(a), low-density lipoprotein (LDL), cholesterol, triglycerides, homocysteine and/or other metabolic risk factors for cardiovascular disease.

Examples of pharmaceutical compositions useful for the prevention or treatment of cardiovascular disease are described, for example, in U.S. Pat. Nos. 5,278,189, 5,650,418, 5,230,996, each of which is incorporated herein in its entirety.

Administration of the compounds of the invention, in pure form or in an appropriate pharmaceutical composition, can be carried out via any of the acceptable modes of administration or pharmaceutically acceptable means of delivery that may serve similar utilities. The modes of administration and pharmaceutically acceptable means of delivery include, but not limited to, oral, nasal, parenteral, topical or transdermal administration or delivery in the form of solid, semi-solid, lyophilized powder, or liquid dosage forms. The dosage forms include tablets, suppositories, pills, soft elastic and hard gelatin capsules, powders, solutions, suspensions, or aerosols, or the like, preferably in unit dosage forms suitable for simple administration of precise dosages.

The compositions may include a conventional pharmaceutical carrier or excipient and a compound of the invention as the active agent, and in addition, may include other medicinal agents, pharmaceutical agents, carriers, adjuvants, etc.

The preferred route of administration is oral, using a convenient daily dosage regimen which can be adjusted according to the degree of severity of the disease state to be treated. For such oral administration, a pharmaceutically acceptable composition containing the compounds of the invention, or a pharmaceutically acceptable salt thereof, is formed by the incorporation of any of the normally employed, pharmaceutically acceptable excipients, such as, pharmaceutical grades of mannitol, lactose, starch, pregelatinized starch, magnesium stearate, sodium saccharine, talcum, cellulose ether derivatives, glucose gelatin, sucrose, citrate, propyl gallate, and the like. Such compositions take the form of solutions, suspensions, tablets, pills, capsules, powders, sustained release formulations and the like.

Preferably such compositions will take the form of capsule, caplet, or tablet and therefore will also contain a diluent such as lactose, sucrose dicalcium phosphate, and the like; a disintegrant such as croscarmellose sodium or derivatives thereof; a lubricant such as magnesium stearate and the like; and a binder such as a starch, gum acacia, polyvinylpyrrolidone, gelatin, cellulose ether derivatives, and the like.

The compounds of the invention in pharmaceutically acceptable form are administrated in a therapeutically effective amount which will vary depending upon a variety of factors including the activity of the specific compounds employed; the metabolic stability and length of action of the compounds; the age, body weight, general health, sex and diet of the patient; the mode and time of administration; the rate of excretion; the drug combination; the severity of the particular disease states; and the patient undergoing treatment. Generally, a therapeutically effective daily dose is not less than about 10% and not more than about 200% of the amounts of individual ingredients listed in Table 1. Most preferably, a therapeutically effective daily dose is about 50% identical with the list of components in Table 1.

The following specific examples are provided as a guide to assist in the practice of the invention, and are not intended as a limitation on the scope of the invention.

EXAMPLES

Example 1

This example illustrates the preparation of a representative pharmaceutical composition containing the biochemical compounds listed in the following table (Table 1).

TABLE 1

| Biochemical Substances | Units | Amount |
|---|---|---|
| Ascorbic Acid | mg | 1580 |
| Ascorbyl Palmitate | mg | 620 |
| Beta-, Gamma-, Delta-Tocopherol-Mix | mg | 22 |
| Beta-Carotene | mcg | 999 |
| Biotin | mcg | 165 |
| Calcium Ascorbate | mg | 1050 |
| Calcium Glycinate | mg | 35 |
| Carotenoid-Mix: (α-Carotene, Lutein, Zea-Cryptoxanthin) | mcg | 50 |
| Cholecalciferol | mcg | 3.3 |
| Chromium Glycinate | mcg | 10 |
| Citrus Bioflavonoids | mg | 550 |
| Coenzyme Q 10 | mg | 7 |
| Copper Glycinate | mcg | 330 |
| Cyanocobalamin | mcg | 20 |
| d-Alpha-Tocopherol | mg | 154 |
| d-Calcium Pantothenate | mg | 90 |
| Dicalcium Phosphate | mg | 15 |
| Folic Acid | mcg | 490 |
| Inositol | mg | 35 |
| L-Arginine | mg | 40 |
| L-Carnitine | mg | 135 |
| L-Cysteine | mg | 35 |
| L-Lysine | mg | 110 |

TABLE 1-continued

| Biochemical Substances | Units | Amount |
| --- | --- | --- |
| L-Proline | mg | 110 |
| L-Selenomethionine | mcg | 20 |
| Magnesium Ascorbate | mg | 1050 |
| Magnesium Glycinate | mcg | 40 |
| Manganese Chelate | mcg | 1300 |
| Molybdenum Glycinate | mcg | 4 |
| Niacin | mg | 60 |
| Niacinamide | mg | 335 |
| Potassium Chelate | mg | 20 |
| Pycnogenol | mg | 7 |
| Pyridoxine | mg | 20 |
| Riboflavin | mg | 7 |
| Thiamine | mg | 7 |
| Zinc Glycinate | mg | 7 | mg = milligrams
mcg = micrograms

Example 2

To demonstrate the utility of the composition of the invention as therapeutic agents for treating disease states which are alleviated by the reduction of plasma Lp(a) levels, we evaluated the composition of these biochemical compounds for its ability to lowering plasma Lp(a) and other lipoproteins in humans.

We administered the biochemical composition containing the compounds listed in Table 1 in a prospective clinical study with 14 patients. Various clinical parameters were recorded before the administration of the composition. Blood samples were collected via venipuncture at the beginning of the study and plasma levels of various lipoproteins were monitored with ELISA assays.

The ages of this group of 14 patients ranged from 34 to 68 years old. This group of human subjects were clinically classified as polygenic hyperlipidemia. The average plasma level of Lp(a) was 71 mg/dl. The average plasma total cholesterol level was 293 mg/dl. The average plasma LDL-cholesterol level was 195 mg/dl. The average plasma triglyceride level was 193 mg/dl.

These patients received the biochemical compounds listed in Table 1 as a daily dosage. The patients received the compounds of the invention for a period of three months. At the end of the three months after the therapeutic intervention, blood samples were again collected via venipuncture at the end of the study. Plasma concentrations of various lipoproteins were monitored with ELISA assays.

Figure 2:
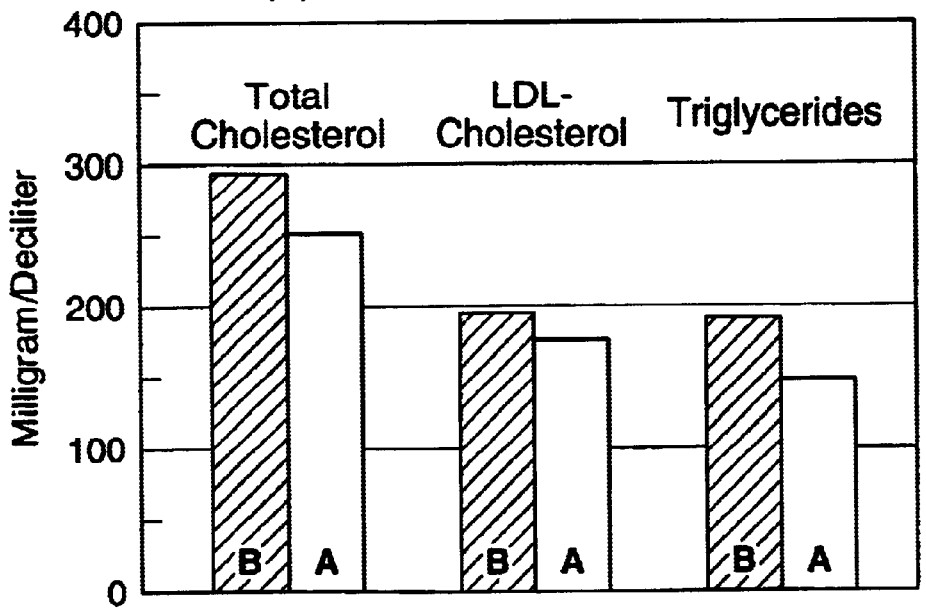
FIG. 2 depicts the change in plasma concentrations of total cholesterol, LDL-cholesterol, and triglycerides in humans before and after 12 weeks of therapy.

Results of the study, as illustrated in FIG. 1 and FIG. 2 demonstrates that the patents, after therapeutic administration of compositions, had led to the following average decrease in plasma levels of.

1. Lp(a) from 71 mg/dl to 64 mg/dl, a decrease of 13%;
2. Total-cholesterol from 293 mg/dl to 252 mg/dl, a decrease of 14%;
3. LDL-cholesterol from 195 mg/dl to 176 mg/dl, a decrease of 10%; and
4. Triglycerides from 193 mg/dl to 151 mg/dl, a decrease of 22%.

The results are further depicted graphically in FIG. 1 and FIG. 2.

FIG. 1 is a graph for a pilot study conducted with 14 patients with various forms of lipid disorders (hyperlipoproteinemia). Their average lipoprotein(a) levels at study entry were 71 mg/dl (milligrams per deciliter). After therapeutic use of the formula of Table 1 the lipoprotein(a) levels were lowered within 12 weeks to an average of 62 mg/dl. This equals a reduction in the plasma concentration of this risk factor by 13%.

FIG. 2 is a graph showing the lowering effect of the composition of Table 1 on additional risk factors for cardiovascular diseases. Within 12 weeks of therapy the total cholesterol levels decreased on average from 293 mg/dl to 252 mg/dl (−14%), the LDL-cholesterol from 195 mg/dl to 16 mg/dl (−10%) and triglycerides from 193 mg/dl to 151 mg/dl (−22%).

When the chemical compounds of the present invention are combined, the concentration of plasma lipoproteins is significantly reduced. This combined effect is surprising in its effectiveness in lowering the plasma concentration of these lipoproteins as well as the risk of cardiovascular diseases. The lowering of the plasma concentration over the duration of 12 weeks indicates the therapeutic potential of the biochemical composition in controlling chronic elevation of lipoproteins in humans.

While the present invention has been described with reference to the specific embodiments thereof, it should be understood by those skilled in the art that various changes may be made and equivalents may be substituted without departing from the true spirit and scope of the invention. One of the ordinary skill in the art would appreciate that the effective amounts of the biochemical compounds may vary depending on the variations in patients, durations of treatment etc. Modifications may be made to adapt a particular situation, and composition of matter. A number of embodiments of the invention have been described in the present application; nevertheless, it will be understood all such modifications are intended to be within the scope of the following claims.

What is claimed is:

1. The composition of biochemical substances consisting of asorbic acid, ascorbyl palmitate, beta-, gamma-, delta-tocopherol-mix, beta-carotene, biotin, calcium ascorbate, calcium glycinate, caroteinoid mix: (2-Lasotene, Latein, Zea-Cryptoxanthin), cholecalciferol chromium glycinate, citrus bioflavonoids, coenzyme Q10, copper glycinate, cyanocobalamin, d-alpha-tocopherol, di-calcium pantothenate, dicalcium phosphate, folic acid, inositol, L-arginine, L-camitine, L-cysteine, L-lysine, L-proline, L-selenomethionine, magnesium ascorbate, magnesium glycinate, manganese chelate, molybdenum glycinate, niacin, niacinamide, potassium chelate, pycnogenol, pyridoxine, riboflavin, thiamine, and zinc glycinate, wherein the composition is in therapeutically effective amounts to lower plasma concentration of a lipoprotein in a mammal.

2. The composition of biochemical substances according to claim 1, wherein the lipoprotein is selected from the group consisting of total cholesterol, LDL-cholesterol, triglycerides, low density lipoprotein and homocysteine.

3. The composition of biochemical substances according to claim 1, wherein the lipoprotein is Lp(a).

4. The composition of biochemical substances according to claim 1, wherein the mammal is a human.

5. The composition of biochemical substances as in any one of claims 1–4, wherein the composition is provided to a human in form of tablets, pills, injections, infusions, inhalations, suppositories or other pharmaceutically acceptable means of delivery.

6. The composition of claim 1, wherein ascorbic acid is 1580 mg, niacin is 60 mg, lysine is 110 mg, and proline is 110 mg.

* * * * *